(12) United States Patent
Weber et al.

(10) Patent No.: US 11,583,672 B2
(45) Date of Patent: Feb. 21, 2023

(54) GLASS IMPELLER FOR A BLOOD PUMP

(71) Applicant: Boston Scientific Scimed Inc, Maple Grove, MN (US)

(72) Inventors: Jan Weber, Maastricht (NL); Matthew Boyer, Columbia Heights, MN (US); Umang Anand, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 160 days.

(21) Appl. No.: 17/004,110

(22) Filed: Aug. 27, 2020

(65) Prior Publication Data
US 2021/0060223 A1 Mar. 4, 2021

Related U.S. Application Data

(60) Provisional application No. 62/894,010, filed on Aug. 30, 2019.

(51) Int. Cl.
*A61M 60/419* (2021.01)

(52) U.S. Cl.
CPC ....... *A61M 60/419* (2021.01); *A61M 2205/02* (2013.01)

(58) Field of Classification Search
CPC ...... A61M 2205/02; A61M 2205/0222; A61M 60/216; A61M 60/205; A61M 60/221; A61M 60/804; A61M 60/806; A61M 60/419; A61M 60/13; F04D 7/00; F04D 13/0606; F04D 29/007; F04D 29/02; F04D 29/026
See application file for complete search history.

(56) References Cited

U.S. PATENT DOCUMENTS

| | | | | |
|---|---|---|---|---|
| 3,938,913 | A * | 2/1976 | Isenberg | F16C 32/047 417/356 |
| 5,211,546 | A * | 5/1993 | Isaacson | F04D 13/0646 604/151 |
| 8,002,518 | B2 * | 8/2011 | Woodard | F01D 25/22 415/104 |
| 8,177,703 | B2 * | 5/2012 | Smith | A61M 60/422 600/16 |

* cited by examiner

*Primary Examiner* — Kenneth Bomberg
*Assistant Examiner* — Adam W Brown
(74) *Attorney, Agent, or Firm* — Faegre Drinker Biddle & Reath LLP

(57) ABSTRACT

A blood pump includes an impeller assembly housing; and an impeller assembly disposed within the impeller assembly housing. The impeller assembly includes an impeller having a main body, at least one impeller blade extending outwardly therefrom, and a skirt disposed around at least a portion of the main body. At least a portion of the at least one impeller blade is disposed between the main body and an inner surface of the skirt.

14 Claims, 6 Drawing Sheets

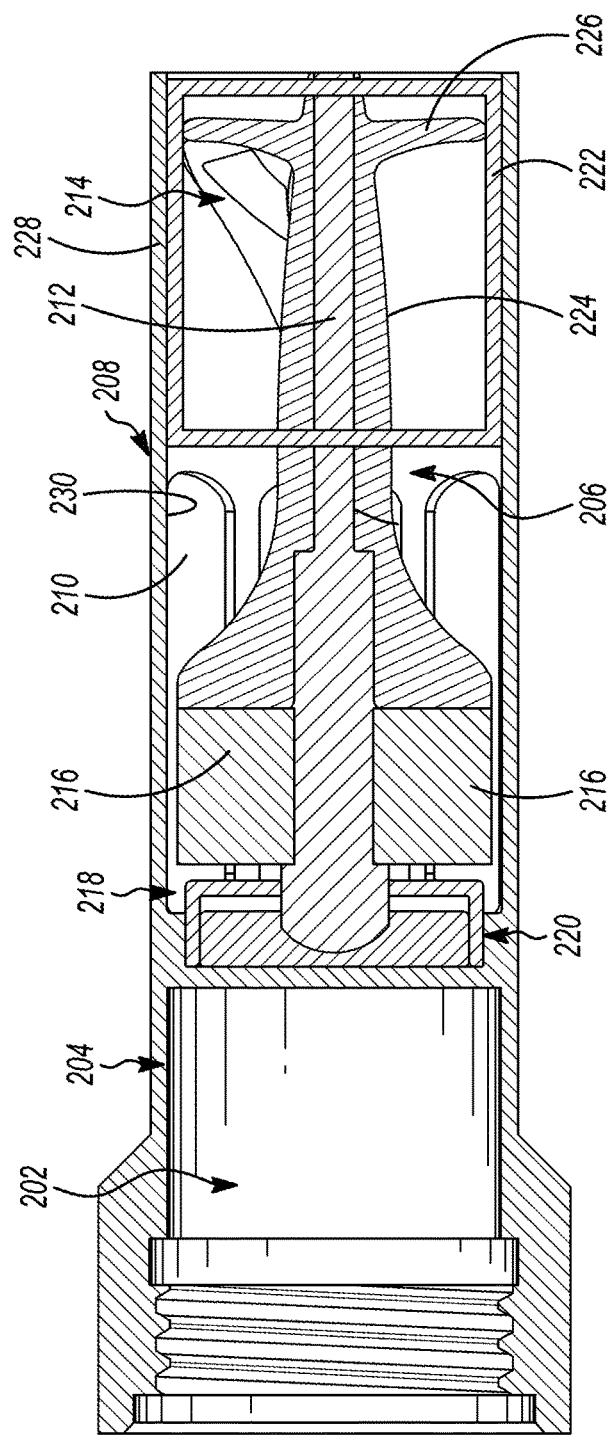
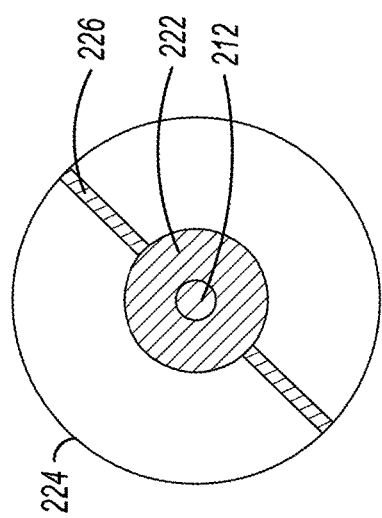
FIG. 2A
FIG. 2B

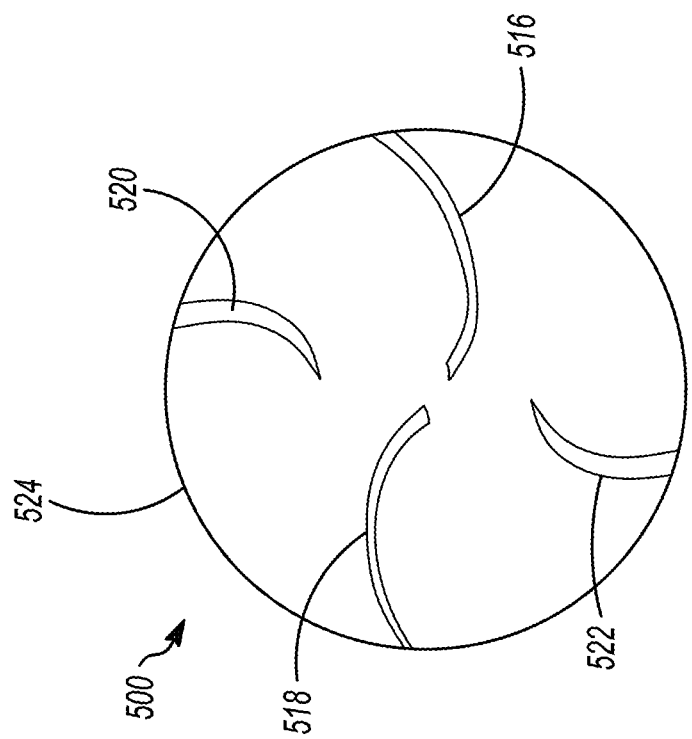
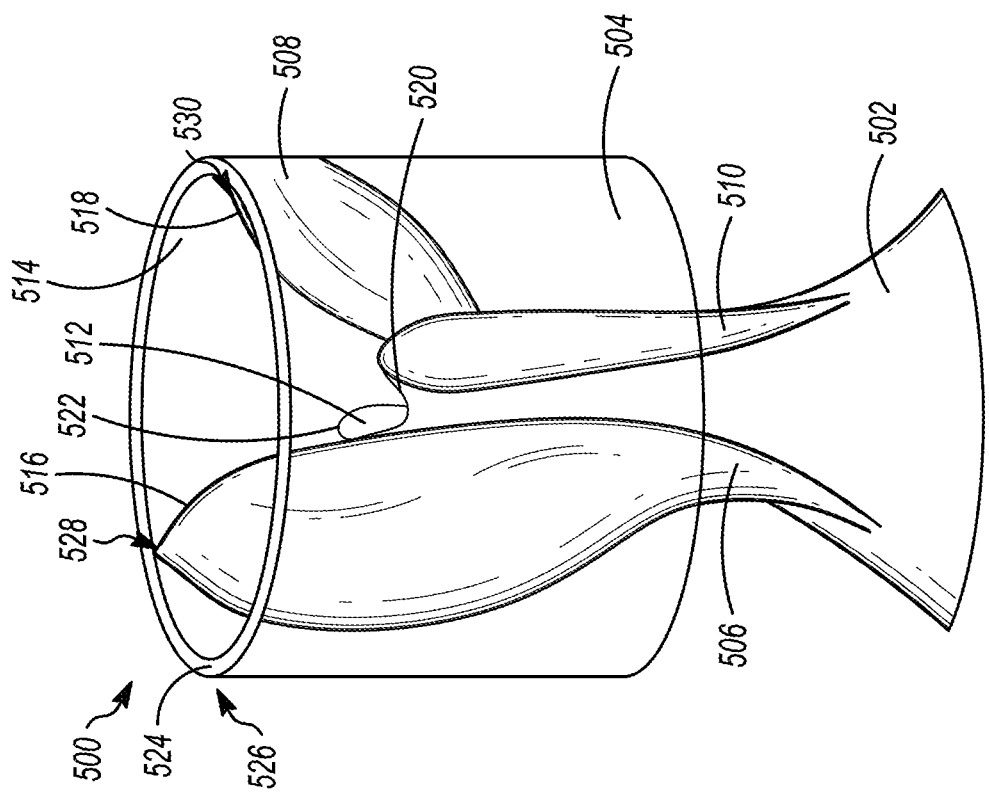

GLASS IMPELLER FOR A BLOOD PUMP

CROSS REFERENCE TO RELATED APPLICATION

This application claims priority to Provisional Application No. 62/894,010, filed Aug. 30, 2019, which is herein incorporated by reference in its entirety.

TECHNICAL FIELD

The present disclosure relates to percutaneous circulatory support devices. More specifically, the disclosure relates to impellers used in percutaneous circulatory support devices.

BACKGROUND

Percutaneous circulatory support devices such as blood pumps typically provide circulatory support for up to approximately three weeks of continuous use. Wear at bearing surfaces can limit the lifetime of the devices. Additionally, heat generation and mechanical interactions with the blood at the bearing and impeller-blade surface can lead to hemolysis, which can further lead to health complications such as anemia, requiring blood transfusions. Additionally, increased friction at the blood-surface interface may require higher motor power to maintain the pump output, which may warrant a bigger motor size.

SUMMARY

In an Example 1, a blood pump, comprising: an impeller assembly housing; and an impeller assembly disposed within the impeller assembly housing, the impeller assembly comprising an impeller having a main body, at least one impeller blade extending outwardly therefrom, and a skirt disposed around at least a portion of the main body, wherein at least a portion of the at least one impeller blade is disposed between the main body and an inner surface of the skirt.

In an Example 2, the blood pump of Example 1, wherein the at least one impeller blade is connected to the skirt.

In an Example 3, the blood pump of either of Examples 1 or 2, wherein the impeller is one solid piece.

In an Example 4, the blood pump of any of Examples 1-3, wherein the impeller is made of chemically strengthened glass.

In an Example 5, the blood pump of any of Examples 1-4, wherein the impeller assembly is configured to rotate within the impeller assembly housing.

In an Example 6, the blood pump of Example 5, the skirt comprising an outer surface configured to be disposed adjacent an inner surface of the impeller assembly housing.

In an Example 7, the blood pump of any of Examples 1-6, the skirt having a proximal end and a distal end, the distal end having a distal outer edge, wherein the at least one impeller blade includes a leading edge that is at least partially coplanar with at least a portion of the distal outer edge.

In an Example 8, the blood pump of Example 7, wherein at least a portion of the leading edge is coplanar with the distal outer edge.

In an Example 9, the blood pump of either of Examples 7 or 8, wherein the leading edge extends radially inward from an inner surface of the skirt to an outer surface of the main body.

In an Example 10, the blood pump of any of Examples 7-9, wherein a first portion of the leading edge is coplanar with at least a portion of the distal outer edge, and wherein a second portion of the leading edge slopes axially toward the proximal end of the skirt.

In an Example 11, the blood pump of Example 10, the main body comprising a distal end that is disposed proximal the distal outer edge.

In an Example 12, the blood pump of any of Examples 7-9, wherein the entire leading edge is coplanar with the entire distal outer edge.

In an Example 13, the blood pump of any of Examples 1-12, wherein a width of distal end of the skirt is greater than a width of the proximal end of the skirt.

In an Example 14, the blood pump of any of Examples 1-13, wherein the impeller assembly is maintained in place using only one bearing assembly, the one bearing assembly being disposed at a proximal end of the impeller assembly.

In an Example 15, an impeller fora blood pump, comprising: a main body; at least one impeller blade extending outwardly therefrom; and a skirt disposed around at least a portion of the main body, wherein the impeller is made of glass.

In an Example 16, a blood pump, comprising: an impeller assembly housing; and an impeller assembly disposed within the impeller assembly housing, the impeller assembly comprising an impeller having a main body, at least one impeller blade extending outwardly therefrom, and a skirt disposed around at least a portion of the main body, wherein at least a portion of the at least one impeller blade is disposed between the main body and an inner surface of the skirt.

In an Example 17, the blood pump of Example 16, wherein the at least one impeller blade is connected to the skirt.

In an Example 18, the blood pump of Example 16, wherein the impeller is one solid piece.

In an Example 19, the blood pump of Example 16, wherein the impeller is made of chemically strengthened glass.

In an Example 20, the blood pump of Example 16, wherein the impeller assembly is configured to rotate within the impeller assembly housing.

In an Example 21, the blood pump of Example 20, the skirt comprising an outer surface configured to be disposed adjacent an inner surface of the impeller assembly housing.

In an Example 22, the blood pump of Example 16, the skirt having a proximal end and a distal end, the distal end having a distal outer edge, wherein the at least one impeller blade includes a leading edge that is at least partially coplanar with at least a portion of the distal outer edge.

In an Example 23, the blood pump of Example 22, wherein at least a portion of the leading edge is coplanar with the distal outer edge.

In an Example 24, the blood pump of Example 22, wherein the leading edge extends radially inward from an inner surface of the skirt to an outer surface of the main body.

In an Example 25, the blood pump of Example 22, wherein a first portion of the leading edge is coplanar with at least a portion of the distal outer edge, and wherein a second portion of the leading edge slopes axially toward the proximal end of the skirt.

In an Example 26, the blood pump of Example 25, the main body comprising a distal end that is disposed proximal the distal outer edge.

In an Example 27, the blood pump of Example 22, wherein the entire leading edge is coplanar with the entire distal outer edge.

In an Example 28, the blood pump of Example 16, wherein a width of distal end of the skirt is greater than a width of the proximal end of the skirt.

In an Example 29, the blood pump of Example 16, wherein the impeller assembly is maintained in place using only one bearing assembly, the one bearing assembly being disposed at a proximal end of the impeller assembly.

In an Example 30, an impeller for a blood pump, comprising: a main body; at least one impeller blade extending outwardly therefrom; and a skirt disposed around at least a portion of the main body, wherein the impeller is made of glass.

In an Example 31, the impeller of Example 30, wherein the at least one impeller blade is connected to the skirt.

In an Example 32, the impeller of Example 30, wherein the impeller is one solid piece.

In an Example 33, the impeller of Example 30, the skirt having a proximal end and a distal end, the distal end having a distal outer edge, wherein the at least one impeller blade includes a leading edge that is at least partially coplanar with at least a portion of the distal outer edge.

In an Example 34, the impeller of Example 30, wherein the impeller assembly is maintained in place using only one bearing assembly, the one bearing assembly being disposed at a proximal end of the impeller assembly.

In an Example 35, a blood pump, comprising: an impeller assembly housing; and an impeller assembly disposed within the impeller assembly housing, the impeller assembly comprising an impeller having a main body, at least one impeller blade extending outwardly therefrom, and a skirt disposed around at least a portion of the main body, wherein at least a portion of the at least one impeller blade is disposed between the main body and an inner surface of the skirt, wherein the impeller is made of glass.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIG. 2A depicts a perspective view of an illustrative percutaneous mechanical circulatory support device, in accordance with embodiments of the subject matter disclosed herein.

FIG. 2B depicts a cross-sectional end view of the circulatory support device depicted in FIG. 2A, in accordance with embodiments of the subject matter disclosed herein.

FIG. 5A is a perspective view depicting another illustrative impeller, in accordance with embodiments of the subject matter disclosed herein.

FIG. 5B is a schematic end view of the impeller depicted in FIG. 5A, in accordance with embodiments of the subject matter disclosed herein.

Figure 1:
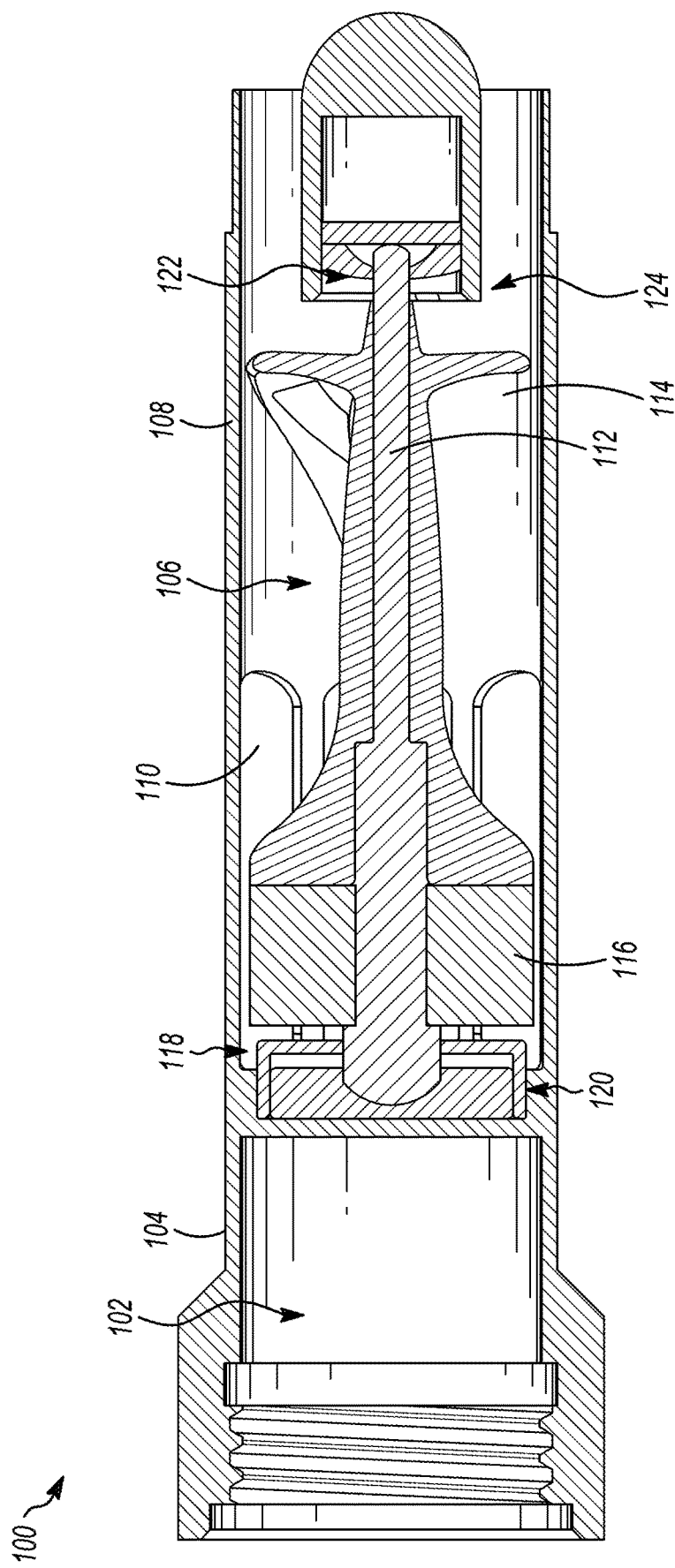
FIG. 1 depicts a cross-sectional side view of a portion of an illustrative percutaneous mechanical circulatory support device (also referred to herein, interchangeably, as a "blood pump"), in accordance with prior designs.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

FIG. 1 depicts a cross-sectional side view of a portion of an illustrative percutaneous mechanical circulatory support device 100 (also referred to herein, interchangeably, as a "blood pump"), in accordance with prior designs. As shown in FIG. 1, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures 110 defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

As shown in FIG. 1, the impeller assembly 106 includes a drive shaft 112 and an impeller 114 coupled thereto, where the drive shaft 112 is configured to rotate with the impeller 114. As shown, the drive shaft 112 is at least partially disposed within the impeller 114. In embodiments, the drive shaft 112 may be made of any number of different rigid materials such as, for example, steel, titanium alloys, cobalt chromium alloys, nitinol, high-strength ceramics, and/or the like. The impeller assembly 106 further includes an impeller rotor 116 coupled to, and at least partially surrounding, the drive shaft 112. The impeller rotor 116 may be any type of magnetic rotor capable of being driven by a stator (not shown) that is part of the motor 102. In this manner, as a magnetic field is applied to the impeller rotor 116 by the stator in the motor 102, the rotor 116 rotates, causing the drive shaft 112 and impeller 114 to rotate.

As shown, the impeller assembly 106 is maintained in its orientation by the drive shaft 112, which is retained, at a first end 118, by a first (proximal) bearing assembly 120 and, at a second end 122, by a second (distal) bearing assembly 124. According to embodiments, the first bearing assembly 120 and the second bearing assembly 124 may include different types of bearings. According to embodiments, the first bearing assembly 120 and/or the second bearing assembly 124 may include lubrication, while, in other embodiments, one and/or the other may not include lubrication. As the terms "proximal" and "distal" are used herein, "proximal" refers to the general direction opposite that of insertion—that is, the direction in which one would travel along the device to exit the subject's body; whereas distal refers to the general direction of implantation—that is, the direction in which one would travel along the device to reach the end of the device that is configured to advance into the subject's body.

The prior impeller is generally made out of PEEK using conventional machining and subsequent polishing. The impeller needs to be strong, precisely dimensioned and smooth to avoid damage to the blood cells. There are significant limitations regarding the freedom of design because of this manufacturing process. Although 3D printing might give much broader freedom regarding shapes, one has to realize that complex shapes will make polishing more difficult or even impossible. The impeller 114 is furthermore mounted in a metal housing 108. Studies of the flowlines though the prior pump have revealed that there is quite a bit of shear force between the rotating fluid and the static inner wall of the housing 108.

Furthermore, as described above, the impeller 114 is supported by the two endpoints, allowing it to rotate. The proximal bearing 120 dissipates both axial and radial force, while the distal bearing 124 just holds the impeller 114 in radial position. Having the distal bearing 124 in place requires axial space for mounting and introduces flow resistance. Embodiments of the disclosure include a blood pump having only a proximal bearing (the distal bearing is not included). This may reduce flow resistance and facilitate shortening the overall construction of the blood pump, which may enable the device to better fit within an arching aorta.

FIG. 2A depicts a cross-sectional side view of a portion of an illustrative percutaneous mechanical circulatory support device 200 (also referred to herein, interchangeably, as a "blood pump"); and FIG. 2B depicts a cross-sectional end view of the circulatory support device 200 depicted in FIG. 2A, in accordance with embodiments of the subject matter disclosed herein. According to embodiments, a number of various components of the circulatory support device 200 may be the same as, or similar to, corresponding components of the circulatory support device 100 depicted in FIG. 1.

As shown in FIG. 2A, the circulatory support device 200 includes a motor 202 disposed within a motor housing 204. The motor 202 is configured to drive an impeller assembly 206 to provide a flow of blood through the device 200. The impeller assembly 206 is disposed within an impeller assembly housing 208, which includes a number of outlet apertures 210 defined therein. According to embodiments, the motor housing 204 and the impeller assembly housing 208 may be integrated with one another. In other embodiments, the motor housing 204 and the impeller assembly housing 208 may be separate components configured to be coupled together, either removeably or permanently.

A controller (not shown) is operably coupled to the motor 202 and is configured to control the motor 202. The controller may be disposed within the motor housing 204 in embodiments, or, in other embodiments, may be disposed outside the housing 204 (e.g., in a catheter handle, independent housing, etc.). In embodiments, the controller may include multiple components, one or more of which may be disposed within the housing 204. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 2A, the impeller assembly 206 includes a drive shaft 212 and an impeller 214 coupled thereto, where the drive shaft 212 is configured to rotate with the impeller 214. As shown, the drive shaft 212 is at least partially disposed within the impeller 214. In embodiments, the drive shaft 212 may be made of any number of different rigid materials such as, for example, steel, titanium alloys, cobalt chromium alloys, nitinol, high-strength ceramics, and/or the like. The impeller assembly 206 further includes an impeller rotor 216 coupled to, and at least partially surrounding, the drive shaft 212. The impeller rotor 216 may be any type of magnetic rotor capable of being driven by a stator (not shown) that is part of the motor 202. In this manner, as a magnetic field is applied to the impeller rotor 216 by the stator in the motor 202, the rotor 216 rotates, causing the drive shaft 212 and impeller 214 to rotate. In embodiments, the impeller assembly 206 may be configured to be directly driven by the motor 202. That is, for example, instead of having a rotor/stator configuration, the motor 202 may be configured to cause the drive shaft 212 to rotate, which thereby causes the impeller 214 to rotate.

As shown, the impeller assembly 206 is maintained in its orientation by the drive shaft 212, which is retained, at a first end 218, by a proximal bearing assembly 220. According to embodiments, the bearing assembly 220 may include lubrication, and may be, or include, any number of different types of bearings. In contrast to prior designs (e.g., as shown in FIG. 1), embodiments of the device 200 disclosed herein may omit a distal bearing assembly that is independent of the impeller assembly 206. Instead, as shown, the impeller 214 includes a skirt 222 disposed around at least a portion of a main body 224. One or more impeller blades 226 are connected to the skirt 222 and the main body 224 and are disposed at least partially between the skirt 222 and the main body 224. According to embodiments, the skirt 222 may include an outer surface that is configured to be disposed adjacent an inner surface 230 of the impeller assembly housing 208 such that the skirt 222 functions as a bearing, maintaining the position of the impeller 214 within the impeller assembly housing 208. In embodiments, since both surfaces (the blades and surrounding tubing (skirt)) are all rotating at the same speed and in the same direction, there may be much less shear force on the flow, thereby producing less damage to the blood.

According to embodiments, the impeller 214 may be made of glass such as, for example, by using selective laser etching to fashion the impeller 214 all in one piece from a glass block. Selective laser-induced etching (SLE) is a two-step process to produce 3D structures in transparent materials (also known as ISLE: In-volume selective laser induced etching—to distinguish our process from laser ablation). In a first step, the transparent fused silica glass is modified internally by laser radiation to increase the chemical etchability locally. To prevent the formation of cracks in the brittle material, short pulse duration (fs-ps) and a small focal volume (a few μm3) may be used. The focus is scanned inside the glass to modify a 3D connected volume with contact to the surface of the workpiece.

In a second step, the modified material is selectively removed by wet chemical etching resulting in the development of the 3D product. The selectivity is the ratio of the etching rate of the modified material and the etching rate of the untreated material. The selectivity in fused silica glass is larger than 500:1, resulting in long fine channels with small conicity. Therefore, by the SLE-technique, complex 3D cavities can be produced, like micro fluidic structures and micro structures 3D parts. According to embodiments, advantages of SLE are the large precision (~1 µm), no debris, true 3D capability and the high processing speed using micro scanners.

A prior polishing process for glass materials uses disc or point tools and a polishing liquid, which is applied to the work piece. In that process, large amounts of waste can arise. By means of laser polishing, glass surfaces can be polished without creating waste, independent of the surface form and with the same tool. In addition, the processing time of laser polishing is smaller by a factor of up to 100 times. It can attain a surface roughness of quartz glass down to Root Mean Square roughness (RMS) <5 nm (1×1 mm2 measuring field) and micro roughness down to RMS<0.4 nm (50×70 µm2 measuring field). Applications for laser polishing of glass surfaces are, among others, lighting optics, for which the values currently achieved are sufficient. The process can be applied to nearly all kinds of glass, whereas higher process speeds are reached for low-melting glasses. The very low roughness values compared to the PEEK impeller designs (RMS of roughly 100 nm) results in a much lower friction on the blood, hence a reduction in hemolysis.

In embodiments, impellers described herein may be made of chemically strengthened glass. Chemically strengthened glass is a type of glass that has increased strength as a result of a post-production chemical process. Chemically strengthened glass is typically six to eight times the strength of float glass. The glass is chemically strengthened by a surface finishing process. Glass is submersed in a bath containing a potassium salt (typically potassium nitrate) at 300° C. (572° F.). This causes sodium ions in the glass surface to be replaced by potassium ions from the bath solution. These potassium ions are larger than the sodium ions and therefore wedge into the gaps left by the smaller sodium ions when they migrate to the potassium nitrate solution. This replacement of ions causes the surface of the glass to be in a state of compression and the core in compensating tension. The surface compression of chemically strengthened glass may reach up to 690 MPa.

The strengthening mechanism depends on the fact that the compressive strength of glass is significantly higher than its tensile strength. With both surfaces of the glass already in compression, it takes a certain amount of bending before one of the surfaces can even go into tension. More bending is required to reach the tensile strength. The other surface simply experiences more and more compressive stress. But since the compressive strength is so much larger, no compressive failure is experienced. There also exists a more advanced two-stage process for making chemically strengthened glass, in which the glass article is first immersed in a sodium nitrate bath at 450° C. (842° F.), which enriches the surface with sodium ions. This leaves more sodium ions on the glass for the immersion in potassium nitrate to replace with potassium ions. In this way, the use of a sodium nitrate bath increases the potential for surface compression in the finished article. Chemical strengthening results in a strengthening similar to toughened glass. However, the process does not use extreme variations of temperature and therefore chemically strengthened glass has little or no bow or warp, optical distortion or strain pattern. This differs from toughened glass, in which slender pieces can be significantly bowed.

According to embodiments, by using aspects of the manufacturing process described above to produce blood pump impellers made of glass, the impellers may be designed to have any number of different shapes, optimized for hydrodynamic performance, and/or the like. Examples of some illustrative design concepts are described below with respect to FIG. 3 and FIG. 4.

The illustrative circulatory support device 200 shown in FIGS. 2A and 2B is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIGS. 2A and 2B may be, in embodiments, integrated with various ones of the other components depicted therein (and/or components not illustrated), all of which are considered to be within the ambit of the present disclosure.

Figure 3:
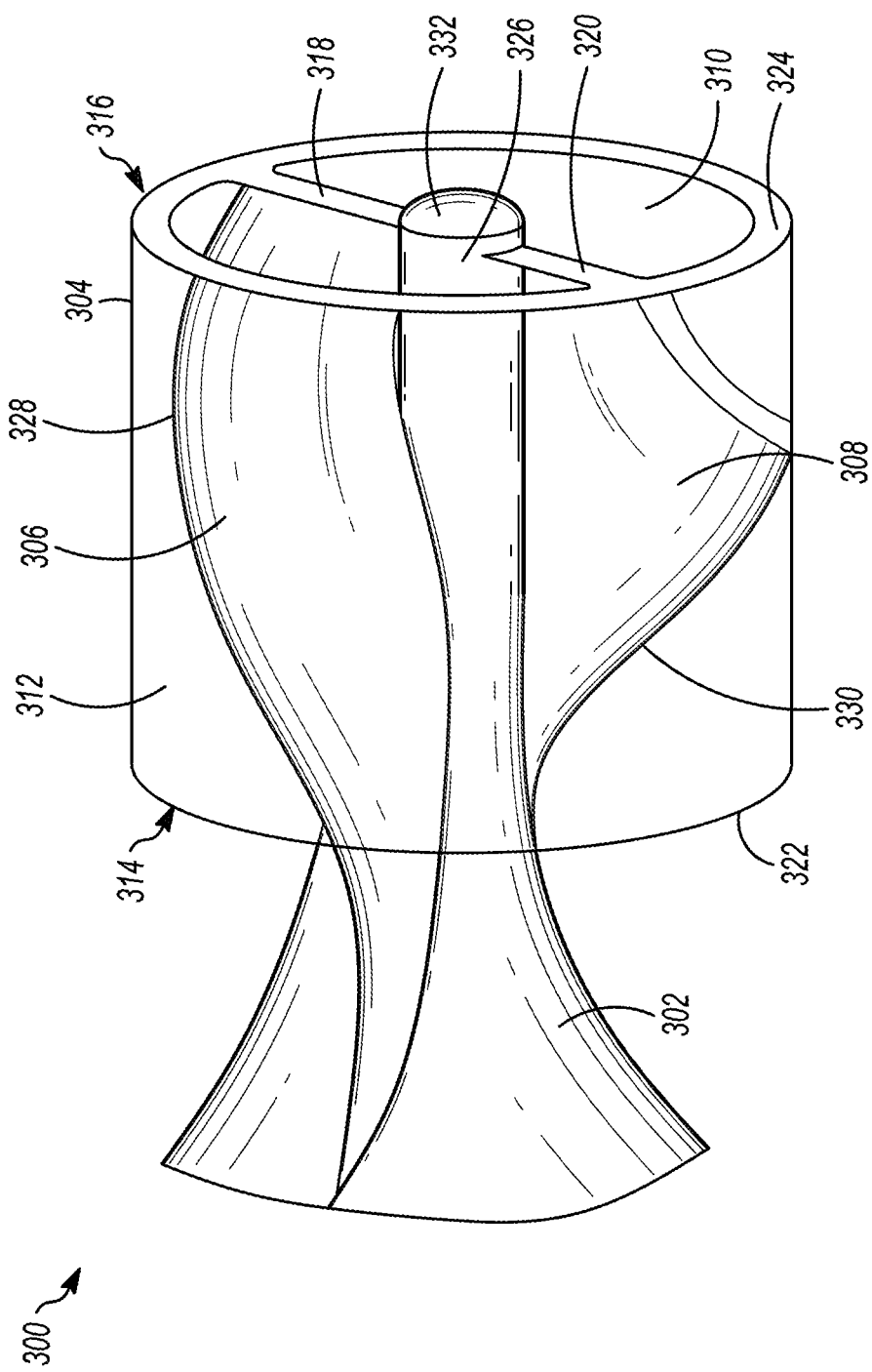
FIG. 3 is a perspective view of an illustrative impeller, in accordance with embodiments of the subject matter disclosed herein.

FIG. 3 is a perspective view of an illustrative impeller 300, in accordance with embodiments of the subject matter disclosed herein. According to embodiments, the impeller 300 may be made from glass such as, for example, by using aspects of a manufacturing processes described herein, and may be, or be similar to, the impeller 214 described. As shown in FIG. 3, the impeller 300 includes a main body 302 and a skirt 304 disposed around at least a portion of the main body 302. A first impeller blade 306 and a second impeller blade 308 extend outwardly from the main body 302. Embodiments of the impeller may incorporate as shown in FIG. 3, at least a portion of each of the two impeller blades 306 and 308 is disposed between the main body 302 and an inner surface 310 of the skirt 304. Each of the impeller blades 306 and 308 is connected to the skirt 304. In embodiments, the impeller blades 306 and 308 may be connected to the skirt 304 at various points. The skirt 304 also includes an outer surface 312 configured to be disposed adjacent an inner surface of an impeller assembly housing (not shown).

In the illustrated embodiments, the skirt 304 includes a cylinder having a first (proximal) end 314 and a second (distal) end 316. The inner and outer surfaces 310 and 312 extend between the first and second ends 314 and 316. In other embodiments, the skirt 304 may be tapered such that a diameter of the skirt at one end is larger than the diameter at the other end. For example, in embodiments, the diameter of the skirt 304 may be greater at or near the distal end 316 than the diameter of the skirt 304 at or near the proximal end 314. In embodiments, the skirt may be configured, as illustrated, to have a circular radial cross section, while, in other embodiments, the skirt 304 may be configured to have a radial cross section of any number of other shapes, so long as the shape of the skirt does not prevent the skirt from rotating within an impeller housing.

Each of the impeller blades 306 and 308 includes a leading edge 318, 320, respectively. The leading edge 318 is the distal-most edge of the impeller blade 306, and the leading edge 320 is the distal-most edge of the impeller blade 308. That is, the leading edges 318 and 320 are the edges of the impeller blades 306 and 308, respectively, that first encounter blood as it flows into the device and across the impeller 300. As shown in FIG. 3, the skirt 304 includes a proximal outer edge 322 at the proximal end of the skirt 304, and a distal outer edge 324 at the distal end 316 of the skirt 304. In the illustrated embodiments, the entire leading edge 318 of the first impeller blade 306 and the entire leading edge 320 of the second impeller blade 308 each are coplanar with the entire distal outer edge 324 of the skirt 304. In embodiments, one or more of the leading edges 318 and 320 may be at least partially coplanar with at least a portion of the distal outer edge 324 of the skirt 304.

That is, for example, any portion or portions of one or more of the leading edges 318 and 320 (and/or leading edges of other blades not depicted) may be coplanar with one or more portions of the distal outer edge 324 of the skirt 304. Although the distal outer edge 324 of the skirt 304 is illustrated as being entirely within a single plane, embodiments may include a distal outer edge 324 that is curved in any number of configurations such that one or more portions of the outer edge lie in different planes. In other embodiments, one or more of the leading edges 318 and 320 may be connected to the distal outer edge 324, but not have any portion that is coplanar therewith. According to embodiments, one or more of the impeller blades 306 and 308 may connect to the skirt 304 at the distal outer edge 324 and/or any other location on the skirt 304. The impeller blades 306 and 308 are each shown as having a width that is greater near the distal end 316 than the width near the proximal end 314, where the width is the distance between the outer surface 326 of the main body and a trailing edge 328 or 330 of the impeller 306 or 308 respectively, in a direction normal to the outer surface 326. In embodiments, one or more of the impeller blades 306 and 308 may be configured to have a greater width near the proximal end 314 than near the distal end 316, in which case, for example, the impeller blades 306 and/or 308 may be connected to the skirt 304 at or near the proximal end 314. In embodiments, the trailing edge 328 and/or 330 may be integrated with the leading edge 316 and/or 318, respectively.

In embodiments, the leading edge 318 of the impeller 306 extends radially inward from a surface (e.g., the distal outer edge 324, the inner surface 310, etc.) of the skirt 304 to an outer surface 326 of the main body 302. Similarly, the leading edge 320 of the impeller 308 extends radially inward from a surface of the skirt 304 to the outer surface 326 of the main body 302. In embodiments, the leading edge and/or trailing edge of an impeller may be straight and/or curved. That is, for example, the leading edge and/or trailing edge of an impeller blade may be curved radially and/or axially to provide a hydrodynamic shape.

Figure 4:
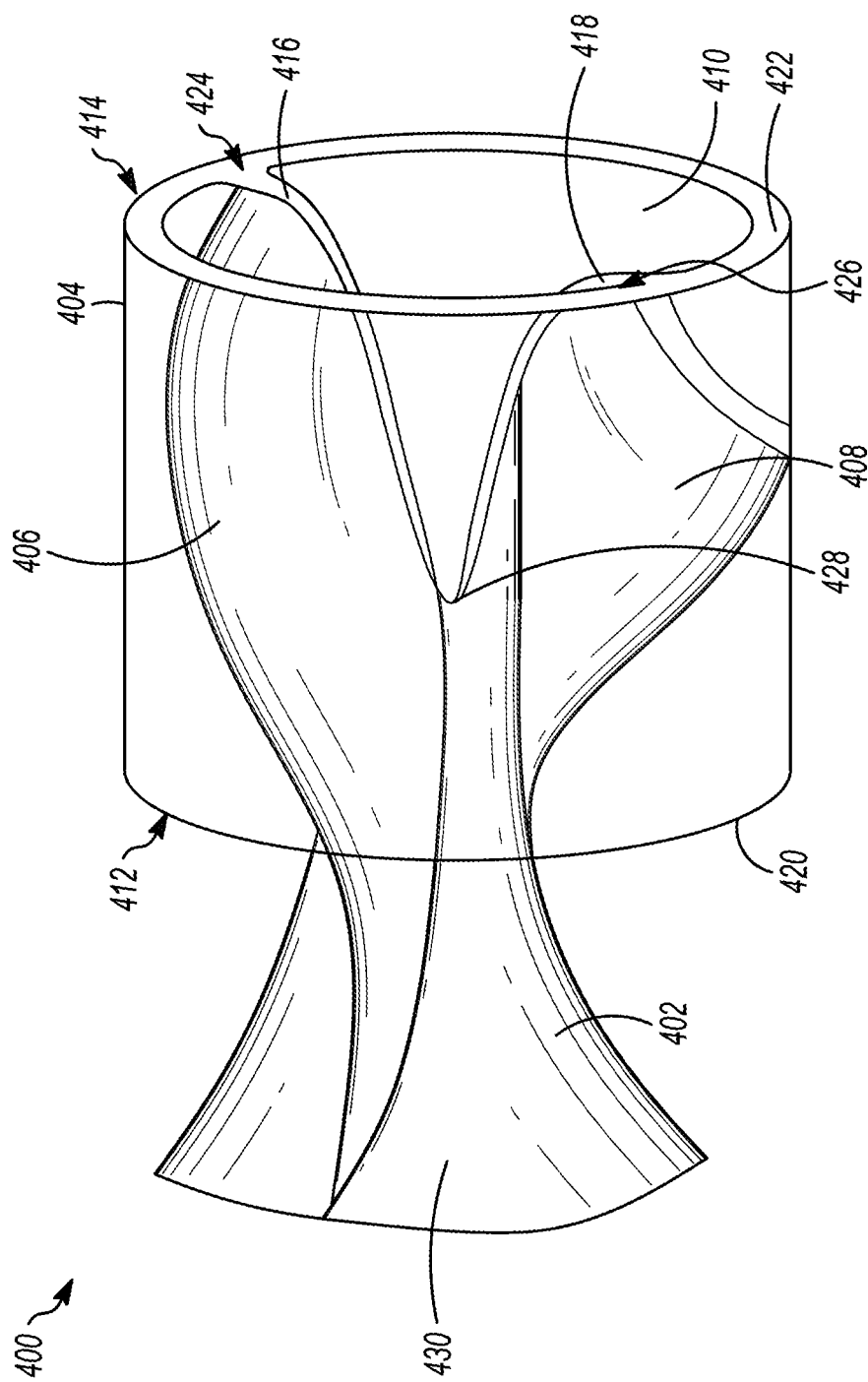
FIG. 4 is a perspective view of another illustrative impeller, in accordance with embodiments of the subject matter disclosed herein.

As shown in FIG. 3, the main body may include a distal end 332 that protrudes axially in the distal direction beyond a plane of the distal outer edge 324 of the skirt 304. The distal end 332 may be rounded, flat, and/or the like. The distal end 332 may, in embodiments, be coplanar with a plane of the distal outer edge 324 of the skirt 304, or, in other embodiments, may be located proximal to one or more planes of the distal outer edge 324. For example, FIG. 4 is a perspective view of another illustrative impeller 400, in accordance with embodiments of the subject matter disclosed herein. According to embodiments, the impeller 400 may be made from glass such as, for example, by using aspects of a manufacturing processes described herein, and may include aspects that are the same as, or similar to, corresponding aspects of the impeller 300 depicted in FIG. 3.

As shown in FIG. 4, the impeller 400 includes a main body 402 and a skirt 404 disposed around at least a portion of the main body 402. A first impeller blade 406 and a second impeller blade 408 extend outwardly from the main body 402. Embodiments may include any number of impeller blades such as, for example, one impeller blade, two impeller blades, three impeller blades, four impeller blades, and/or any other number of impeller blades. As shown in FIG. 4, at least a portion of each of the two impeller blades 406 and 408 is disposed between the main body 402 and an inner surface 410 of the skirt 404. Each of the illustrated impeller blades 406 and 408 is connected to the skirt 404 at one or more locations between a proximal end 412 of the skirt 404 and a distal end 414 of the skirt 404.

Each of the impeller blades 406 and 408 includes a leading edge 416, 418, respectively. The leading edge 416 is the distal-most edge of the impeller blade 406, and the leading edge 418 is the distal-most edge of the impeller blade 408. That is, the leading edges 416 and 418 are the edges of the impeller blades 406 and 408, respectively, that first encounter blood as it flows into the device and across the impeller 400. As shown in FIG. 4, the skirt 404 includes a proximal outer edge 420 at the proximal end 412 of the skirt 404, and a distal outer edge 422 at the distal end 414 of the skirt 404. In the illustrated embodiments, a portion 424 of the leading edge 416 of the first impeller blade 406 and a portion 426 of the leading edge 418 of the second impeller blade 408 each are coplanar with the distal outer edge 422 of the skirt 404.

As shown in FIG. 4, each leading edge 416 and 418 curves in a proximal direction to a distal end 428 of the main body 402. The distal end 428 is disposed proximal to the distal outer edge 422 of the skirt 404. The leading edge 416 of the impeller 406 extends radially inward from a surface (e.g., the distal outer edge 422, the inner surface 410, etc.) of the skirt 404 to an outer surface 430 of the main body 402. Similarly, the leading edge 418 of the impeller 408 extends radially inward from a surface of the skirt 404 to the outer surface 430 of the main body 402.

Although the impeller 400 depicted in FIG. 4 includes two impeller blades, impellers made in accordance with embodiments of the subject matter disclosed herein may have more than two blades. In embodiments, an impeller may have three blades, four blades, five blades, six blades, and/or the like. FIG. 5A is a perspective view depicting another illustrative impeller 500, having four blades, in accordance with embodiments of the subject matter disclosed herein. FIG. 5B is a schematic end view of the impeller 500 depicted in FIG. 5A, in accordance with embodiments of the subject matter disclosed herein. According to embodiments, the impeller 500 may be made from glass such as, for example, by using aspects of a manufacturing processes described herein, and may include aspects that are the same as, or similar to, corresponding aspects of the impeller 300 depicted in FIG. 3 and/or the impeller 400 depicted in FIG. 4.

As shown in FIG. 5A, the impeller 500 includes a main body 502 and a skirt 504 disposed around at least a portion of the main body 502. A first impeller blade 506, a second impeller blade 508, a third impeller blade 510, and a fourth impeller blade 512 extend outwardly from the main body 502. As shown in FIG. 5A, at least a portion of each of the four impeller blades 506, 508, 510, and 512 is disposed between the main body 502 and an inner surface 514 of the skirt 504. Each of the illustrated impeller blades 506, 508, 510, and 512 is connected to the skirt 504.

Each of the impeller blades 506, 508, 510, and 512 includes a leading edge 516, 518, 520, and 522, respectively. The leading edges 516, 518, 520, and 522 include the distal-most edges of the respective impeller blades 506, 508, 510, and 512. That is, the leading edges 516, 518, 520, and 522 are the edges of the impeller blades 506, 508, 510, and 512, respectively, that first encounter blood as it flows into the device and across the impeller 500. As shown in FIG. 5A, the skirt 504 includes a distal outer edge 524 at the distal end 526 of the skirt 504. In the illustrated embodiments, a portion 528 of the leading edge 516 of the first impeller blade 506 and a portion 530 of the leading edge 518 of the second impeller blade 508 each are coplanar with the distal outer edge 524 of the skirt 504, while no portion of either of the distal edges 520 or 522 is coplanar with the distal outer edge 524 of the skirt 504.

As shown in FIGS. 5A and 5B, the impeller blades 506, 508, 510, and 512 may be configured such that the blades include more than one set of blades, in which the blades of each set are axially symmetric with each other, similarly shaped, and/or the like. For example, as shown, the impeller 500 may include a first set of impeller blades that includes the first blade 506 and the third blade 510, and a second set of impeller blades that includes the second blade 508 and the fourth blade 512. As shown, the first blade 506 is axially symmetric to the third blade 510, and the second blade 508 is axially symmetric to the fourth blade 512, but none of the blades of the first set are axially symmetric to any of the blades in the second set. That is, each leading edge 516 and 518 of the first set of impeller blades curves in an axially symmetric direction to the other. Similarly, each leading edge 520 and 522 of the second set of impeller blades curves in an axially symmetric direction to the other. In embodiments, sets of blades may include two blades, three blades, four blades, and/or the like, and an impeller may include any number of distinct sets of impeller blades.

Although each of the impellers 300, 400, and 500 depicted in FIGS. 3, 4, and 5A-5B, respectively, includes a main body through which a central axis (not shown) of the impeller passes, implementation of the manufacturing processes disclosed herein enable creation of impellers having bodies of other configurations. For example, in embodiments, the main body may include a number of different portions or legs, only some of which intersect the central axis. In other embodiments, none of the legs intersect the central axis. An example of such an embodiment is depicted in FIGS. 6A and 6B.

Figure 6B:
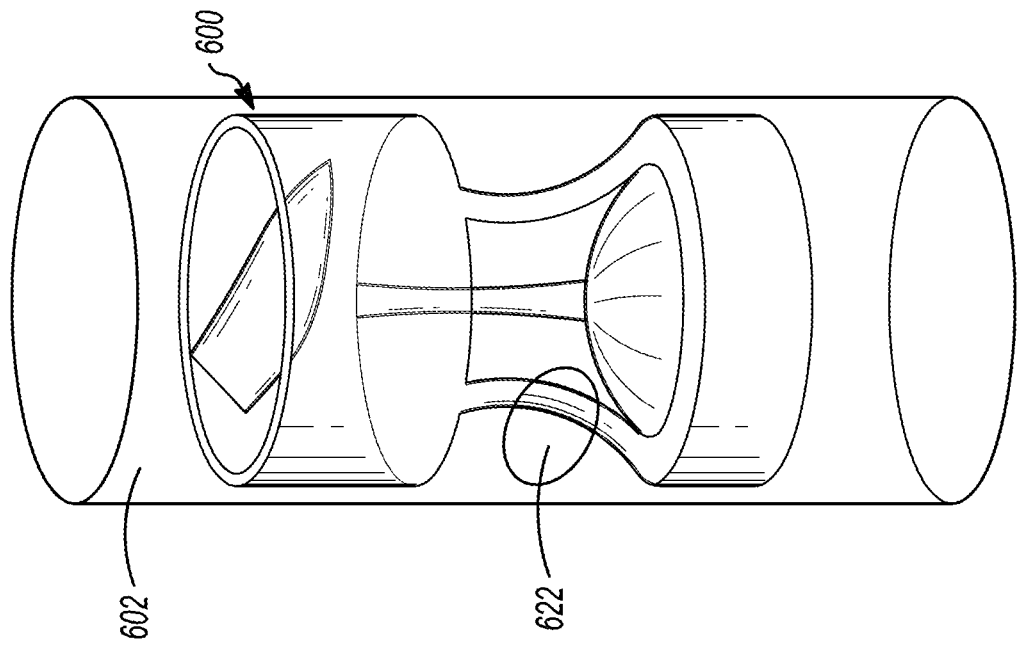
FIG. 6B is a partially cut-away perspective view of the impeller depicted in FIG. 6A, shown disposed within an impeller assembly housing, in accordance with embodiments of the subject matter disclosed herein.
Figure 6A:
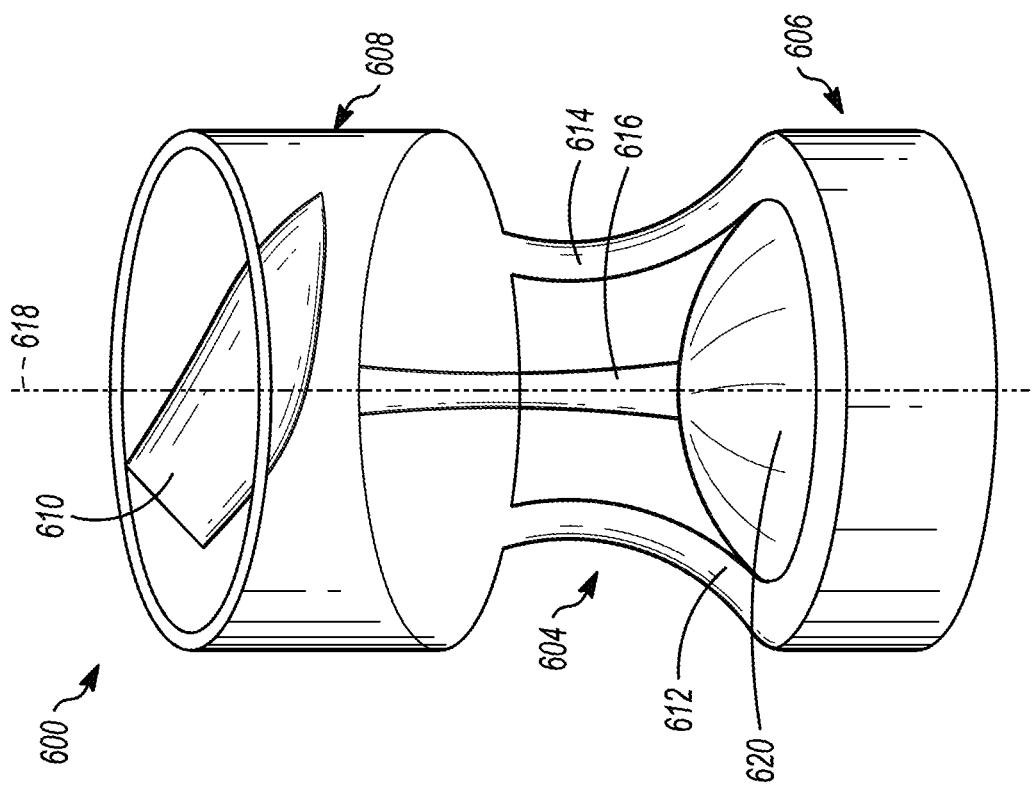
FIG. 6A is a perspective view depicting another illustrative impeller, in accordance with embodiments of the subject matter disclosed herein.

FIG. 6A is a perspective view depicting another illustrative impeller 600, in accordance with embodiments of the subject matter disclosed herein. FIG. 6B is a partially cut-away perspective view of the impeller 600 depicted in FIG. 6A, shown disposed within an impeller assembly housing 602, in accordance with embodiments of the subject matter disclosed herein. According to embodiments, the impeller 600 may be made from glass such as, for example, by using aspects of a manufacturing processes described herein, and may include aspects that are the same as, or similar to, corresponding aspects of the impeller 300 depicted in FIG. 3, the impeller 400 depicted in FIG. 4, and/or the impeller 500 depicted in FIGS. 5A and 5B.

As shown in FIG. 6A, the impeller 600 includes a main body 604 extending between a base portion 606 and a skirt 608. The skirt 608 is disposed around at least one impeller blade 610. As shown in FIG. 6A, the main body 604 includes three individual legs 612, 614, and 616, extending independently from the base portion 606 to the skirt 608, leaving a central space around the central axis 618 open. In embodiments, the base portion 606 may be a housing containing a rotor (magnet), and may include, as shown, a curved distal surface 620 to facilitate blood flow radially away from the central axis 618. Although FIG. 6A shows one blade 610 extending across the skirt perimeter, it will be understood that multiple blades may be positioned axially with respect to one another. Additionally, as shown in FIG. 6A, each of the three legs 612, 614, and 616 is slightly curved inwards, though other designs may be implemented in accordance with embodiments of the subject matter disclosed herein. Further, as shown in FIG. 6B, the flow outlets 622 of the impeller assembly housing 602 may be positioned such that there is space between the legs 612, 614, and 616 and the outlets 622.

The illustrative circulatory support devices 300 shown in FIG. 3, 400 shown in FIG. 4, 500 shown in FIGS. 5A and 5B, and 600 shown in FIGS. 6A and 6B are not intended to suggest any limitation as to the scope of use or functionality of embodiments of the present disclosure. The illustrative circulatory support devices 300, 400, 500, and 600 also should not be interpreted as having any dependency or requirement related to any single component or combination of components illustrated therein. Additionally, various components depicted in FIGS. 3, 4, 5A, 5B, 6A, and 6B may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:
    an impeller assembly housing; and
    an impeller assembly disposed within the impeller assembly housing, the impeller assembly comprising an impeller having a main body, at least one impeller blade extending outwardly therefrom, and a skin disposed around at least a portion of the main body, wherein at least a portion of the at least one impeller blade is disposed between the main body and an inner surface of the skirt, the skirt having a proximal end and a distal end, the distal end having a distal outer edge,
    wherein the at least one impeller blade includes a leading edge, a first portion of the leading edge is coplanar with at least a portion of the distal outer edge, and a second portion of the leading edge slopes axially toward the proximal end of the skirt, and
    wherein the main body comprises a distal end that is disposed proximal the distal outer edge.

2. The blood pump of claim 1, wherein the at least one impeller blade is connected to the skirt.

3. The blood pump of claim 1, wherein the impeller is one solid piece.

4. The blood pump of claim 1, wherein the impeller is made of chemically strengthened glass.

5. The blood pump of claim 1, wherein the impeller assembly is configured to rotate within the impeller assembly housing.

6. The blood pump of claim 5, the skirt comprising an outer surface configured to be disposed adjacent an inner surface of the impeller assembly housing.

7. The blood pump of claim 1, wherein the at least one impeller blade has a width near the distal end of the skirt that is greater than a width of the at least one impeller blade near the proximal end of the skirt.

8. The blood pump of claim 1, wherein the impeller assembly is maintained in place using with only one a proximal bearing assembly and the skirt functioning as a bearing, and the blood pump lacks any'bearing assembly at a distal end of the impeller assembly.

9. An impeller for a blood pump, comprising:
a main body;
at least one impeller blade extending outwardly therefrom; and
a skirt disposed around at least a portion of the main body, the skirt having a proximal end and a distal end, the distal end having a distal outer edge,
wherein the at least one impeller blade includes a leading edge, a first portion of the leading edge is coplanar with at least a portion of the distal outer edge, and a second portion of the leading edge slopes axially toward the proximal end of the skirt,
wherein the main body comprises a distal end that is disposed proximal the distal outer edge, and
wherein the impeller is made of glass.

10. The blood pump of claim 9, wherein the at least one impeller blade is connected to the skirt.

11. The blood pump of claim 9, wherein the impeller is one solid piece.

12. The blood pump of claim 9, the skirt having a proximal end and a distal end, the distal end having a distal outer edge, wherein the at_least one impeller blade includes a leading edge that is at least partially coplanar with at least a portion of the distal outer edge.

13. The blood pump of claim 9, wherein the impeller assembly is maintained in place with a proximal bearing assembly and the skirt functioning as a bearing, and the blood pump lacks any bearing assembly at a distal end of the impeller assembly.

14. A blood pump, comprising:
an impeller assembly housing; and
an impeller assembly disposed within the impeller assembly housing, the impeller assembly comprising an impeller having a main body, at least one impeller blade extending outwardly therefrom, and a skirt disposed around at least a portion of the main body, wherein at least a portion of the at least one impeller blade is disposed between the main body and an inner surface of the skirt, the skirt having a proximal end and a distal end, the distal end having a distal outer edge,
wherein the at least one impeller blade includes a leading edge, a first portion of the leading edge is coplanar with at least a portion of the distal outer edge, and a second portion of the leading edge slopes axially toward the proximal end of the skirt, and
wherein the main body comprises a distal end that is disposed proximal the distal outer edge, and
wherein the impeller is made of glass.

* * * * *